United States Patent
Bärfacker et al.

(10) Patent No.: US 9,260,435 B2
(45) Date of Patent: Feb. 16, 2016

(54) SUBSTITUTED IMIDAZOPYRAZINES AS AKT KINASE INHIBITORS

(71) Applicants: Bayer Intellectual Property GmbH, Monheim (DE); BAYER PHARMA AKTIENGESELLSCHAFT, Berlin (DE)

(72) Inventors: Lars Bärfacker, Oberhausen (DE); William Scott, Guilford, CT (US); Andrea Hägebarth, Berlin (DE); Stuart Ince, Berlin (DE); Hartmut Rehwinkel, Berlin (DE); Oliver Politz, Grünheide/Mark (DE); Roland Neuhaus, Berlin (DE); Ulf Bömer, Glienicke (DE)

(73) Assignee: BAYER PHARMA AKTIENGESELLSCHAFT, Monheim (DE)

( * ) Notice: Subject to any disclaimer, the term of this patent is extended or adjusted under 35 U.S.C. 154(b) by 0 days.

(21) Appl. No.: 14/370,831

(22) PCT Filed: Jan. 8, 2013

(86) PCT No.: PCT/EP2013/050196
§ 371 (c)(1),
(2) Date: Jul. 7, 2014

(87) PCT Pub. No.: WO2013/104610
PCT Pub. Date: Jul. 18, 2013

(65) Prior Publication Data
US 2015/0005309 A1    Jan. 1, 2015

(30) Foreign Application Priority Data
Jan. 10, 2012 (EP) .................................... 12150558

(51) Int. Cl.
*C07D 487/04* (2006.01)
*A61K 45/06* (2006.01)
*A61K 31/4985* (2006.01)

(52) U.S. Cl.
CPC .......... *C07D 487/04* (2013.01); *A61K 31/4985* (2013.01); *A61K 45/06* (2013.01)

(58) Field of Classification Search
CPC ..................................................... C07D 487/04
USPC ........................................... 544/350; 514/249
See application file for complete search history.

(56) References Cited

FOREIGN PATENT DOCUMENTS

WO    WO 2009021990 A1 * 2/2009

* cited by examiner

*Primary Examiner* — Kahsay Habte

(57) ABSTRACT

Compounds of formula (I)

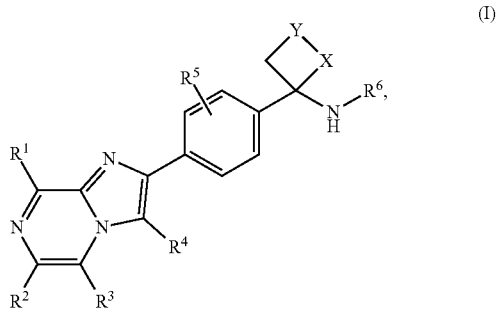

which are effective inhibitors of the Pi3K/Akt pathway, processes for their production and their use as pharmaceuticals.

8 Claims, No Drawings

SUBSTITUTED IMIDAZOPYRAZINES AS AKT KINASE INHIBITORS

FIELD OF APPLICATION OF THE INVENTION

The invention relates to substituted Imidazopyrazine compounds, a process for their production and the use thereof.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

From WO 2008/070016 tricyclic Akt inhibitors are known which are alleged to be unspecific Akt kinase inhibitors. No data for any specific compounds are disclosed. Different Akt inhibitors are disclosed e.g. in WO 2009/021990, WO2010088177, WO2010104705, WO2010114780, WO2011033265, WO2011055115. From WO 2007/096764 bicyclic heteroaryl derivatives generally including imidazo [1,2-a]pyrazines as cannabinoid receptor modulators are known. In their publication, Y. Li et al (Bioorg. Med. Chem. Lett. 2009, 19, 834-836 and cited references therein) detail the difficulty in finding optimal Akt inhibitors. The potential application of Akt inhibitors in multiple disease settings, such as for example, cancer, makes the provision of new, Akt inhibitors still highly desirable.

DESCRIPTION OF THE INVENTION

A solution to the above problem is the provision of improved Akt inhibitors, whereby the current compounds have an improved pharmacokinetic profile. It has now been found that the new substituted Imidazopyrazine compounds, which are described in detail below, are Akt inhibitors with an improved pharmacokinetic profile.

In accordance with a first aspect, the invention relates to compounds of formula (I)

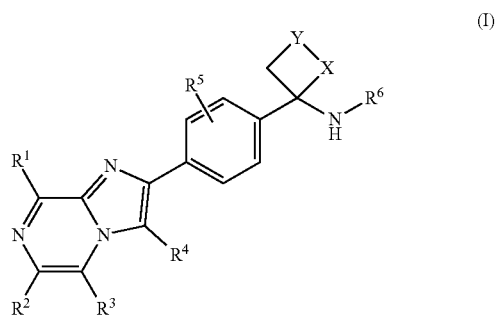

in which
R$^1$ is hydrogen, hydroxy, or
  a group selected from 1-6C-alkyl, 1-6C-alkoxy,
    wherein said group being optionally substituted, one or more times, identically or differently, with a substituent selected from:
      hydroxy, halogen, 1-6C-alkyl, 1-4C-haloalkyl, 1-6C-alkoxy, —NR$^7$R$^8$, cyano, (═O), —C(O)NR$^7$R$^8$, —C(O)OR$^9$, —NHC(O)R$^{19}$, —NHS(O)$_2$R$^{10}$, heteroaryl,
      wherein said substituent can be optionally substituted with 1-6C-alkoxy,
R$^2$ is hydrogen, halogen, C(O)OR$^9$, CO(NR$^7$R$^8$), or
  a 1-6C-alkyl group
    wherein said group is optionally substituted, one or more times, identically or differently, with a substituent selected from:
      hydroxy, halogen, 1-6C-alkyl, 1-4C-haloalkyl, 1-6C-alkoxy, —NR$^7$R$^8$, cyano, —C(O)NR$^7$R$^8$, —C(O)OR$^9$, —NHC(O)R$^{10}$, —NHS(O)$_2$R$^{10}$, —NH-(1-6C-alkylen)-O-(1-6C-alkyl),
R$^3$ is hydrogen, 1-6C-alkyl,
R$^4$ is phenyl optionally substituted by 1-6C-alkyl, halogen, cyano,
R$^5$ is hydrogen, halogen,
R$^6$ is hydrogen, 1-6C-alkyl,
X is —CH$_2$—,
Y is —CH$_2$—, —CH(OH)—,
R$^7$, R$^8$ which can be the same or different, is hydrogen, hydroxy, 3-7C-cycloalkyl or
  a group selected from 1-4C-alkyl, 1-6C-alkoxy, wherein said group is optionally substituted, one or more times, identically or differently, with a substituent selected from:
    halogen, hydroxy, mono- or di-(1-4C-alkylamino), 1-4C-alkoxy, or 3-7C-cycloalkyl or,
  R$^7$ and R$^8$ together with the nitrogen to which they are attached may also form a saturated or unsaturated 3-6C-heterocyclic ring,
    which is optionally substituted by (═O)
R$^9$ is hydrogen, 1-6C-alkyl,
R$^{10}$ is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) according to claim 1, wherein
R$^1$ is hydrogen, hydroxy, 1.-6C-alkyl, 1-6C-alkoxy,
R$^2$ is hydrogen, halogen, 1-6C-alkyl, (CO)OR$^9$, (CO)NR$^7$R$^8$,
R$^3$ is hydrogen,
R$^4$ is phenyl optionally substituted by 1-6C-alkyl, halogen, cyano,
R$^5$ is hydrogen,
R$^6$ is hydrogen,
X is —CH$_2$—,
Y is —CH$_2$—, —CH(OH)—,
R$^7$, R$^8$ which can be the same or different, is hydrogen, hydroxy, or
  a group selected from 1-4C-alkyl, 1-6C-alkoxy, wherein said group is optionally substituted, one or more times, identically or differently, with a substituent selected from:
    halogen, hydroxy, mono- or di-(1-4C-alkylamino), 1-4C-alkoxy, or 3-7C-cycloalkyl, or,
  R$^7$ and R$^8$ together with the nitrogen to which they are attached may also form a saturated or unsaturated 3-6C-heterocyclic ring,
    which is optionally substituted by (═O)
R$^9$ is hydrogen, 1-6C-alkyl,
or an N-oxide, a salt, a tautomer or a stereoisomer of said compound, or a salt of said N-oxide, tautomer or stereoisomer.

Another aspect of the invention are compounds of formula (I) according to claim 1,
wherein
R$^1$ is hydrogen, hydroxy, 1.-6C-alkyl, 1-6C-alkoxy,
R$^2$ is hydrogen, halogen, 1-6C-alkyl, (CO)OR$^9$, (CO)NR$^7$R$^8$,
R$^3$ is hydrogen,
R$^4$ is phenyl
R$^5$ is hydrogen,
R$^6$ is hydrogen,
X is —CH$_2$—,
Y is —CH$_2$—,
R$^7$, R$^8$ which can be the same or different, is hydrogen, 1-4C-alkyl,)
R$^9$ is hydrogen, 1-6C-alkyl,
or an N-oxide, a salt, a tautomer or a stereoisomer of said compound, or a salt of said N-oxide, tautomer or stereoisomer.

A further aspect of the invention are compounds of formula (I) according to claim 1,
wherein,
R$^1$ is hydrogen, hydroxy, 1.-3C-alkyl, 1-3C-alkoxy,
R$^2$ is hydrogen, halogen, 1-3C-alkyl, (CO)O(1-3C-alkyl), (CO)NH$_2$,
R$^3$ is hydrogen,
R$^4$ is phenyl,
R$^5$ is hydrogen,
R$^6$ is hydrogen,
X is —CH$_2$—,
Y is —CH$_2$—,
or an N-oxide, a salt, a tautomer or a stereoisomer of said compound, or a salt of said N-oxide, tautomer or stereoisomer.

Another aspect of the invention are compounds of formula (I) according to claim 1, which is selected from the group consisting of:
2-[4-(1-Aminocyclobutyl)phenyl]-3-phenylimidazo[1,2-a]pyrazin-8-ol,
1-[4-(6,8-Dimethyl-3-phenylimidazo[1,2-a]pyrazin-2-yl)phenyl]cyclobutanamine,
1-[4-(6-Bromo-8-methoxy-3-phenylimidazo[1,2-a]pyrazin-2-yl)phenyl]cyclobutanamine,
1-[4-(6-Ethyl-8-methoxy-3-phenylimidazo[1,2-a]pyrazin-2-yl)phenyl]cyclobutanamine,
Ethyl 2-[4-(1-aminocyclobutyl)phenyl]-3-phenylimidazo[1,2-a]pyrazine-6-carboxylate
2-[4-(1-Aminocyclobutyl)phenyl]-3-phenylimidazo[1,2-a]pyrazine-6-carboxamide.
Methyl 2-[4-(1-aminocyclobutyl)phenyl]-8-methoxy-3-phenylimidazo[1,2-a]pyrazine-6-carboxylate
2-[4-(1-Aminocyclobutyl)phenyl]-8-methoxy-3-phenylimidazo[1,2-a]pyrazine-6-carboxamide.

Another aspect of the invention are an N-oxide, a salt, a tautomer or a stereoisomer of the compound of formula (I) as specified in the table above, or a salt of said N-oxide, tautomer or stereoisomer of these compounds.

One aspect of the invention are compounds of formula (I) as described in the examples as characterized by their names in the title as claimed in claim 5 and their structures as well as the subcombinations of all residues specifically disclosed in the compounds of the examples.

One aspect of the present invention are the compounds disclosed in the examples as well as the intermediates as used for their synthesis.

Another aspect of the invention is intermediate III wherein all residues are defined as in claims 1-4 as well as below the reaction scheme I.

If embodiments of the invention as disclosed herein relate to compounds of formula (I), it is understood that those embodiments refer to the compounds of formula (I) as disclosed in the claims and the examples.

Another aspect of the present invention are compounds of formula (I) wherein
wherein
$R^1$ is hydrogen, hydroxy, 1-6C-alkyl, 1-6C-alkoxy.

Another aspect of the invention relates to compounds of formula (I), wherein
$R^1$ is hydrogen, hydroxy, 1-3C-alkyl, 1-3C-alkoxy.

A further aspect of the invention are compounds of formula (I)
$R^1$ is hydrogen, hydroxy, methyl, methoxy.

One aspect of the invention relates to compounds of formula (I), wherein
$R^1$ is 1-6C-alkyl, especially 1-3C-alkyl, whereby said alkyl is unsubstituted.

Another aspect of the invention are compounds of formula (I)
$R^2$ is hydrogen, halogen, 1-6C-alkyl, (CO)OR$^9$, (CO)NR$^7$R$^8$.

A further aspect of the invention are compounds of formula (I)
wherein
$R^2$ is hydrogen, halogen, 1-3C-alkyl, (CO)O(1-3Calkyl), (CO)NR$^7$R$^8$.

Another aspect of the invention are compounds of formula (I)
wherein $R^2$ is hydrogen, halogen, 1-3C-alkyl, (CO)O(1-3Calkyl), (CO)NR$^7$R$^8$.

A further aspect of the invention are compounds of formula (I) wherein
$R^2$ is hydrogen, halogen, 1-3C-alkyl, (CO)O(1-3Calkyl), (CO)NH$_2$.

One aspect of the invention relates to compounds of formula (I), wherein
$R^2$ is 1-6C-alkyl, especially 1-3C-alkyl, more specifically methyl or ethyl,
whereby said alkyl is unsubstituted.

A further aspect of the invention are compounds of formula (I) wherein
$R^2$ is hydrogen, bromine, methyl, ethyl, —C(O)—OCH$_3$, —C(O)—OCH$_2$CH$_3$, —C(O)—NH$_2$.

Another aspect of the invention are compounds of formula (I), wherein
$R^3$ is hydrogen.

Another aspect of the invention are compounds of formula (I), wherein
$R^4$ is unsubstituted phenyl.

Another aspect of the invention are compounds of formula (I), wherein
$R^5$ is hydrogen.

Another aspect of the invention are compounds of formula (I), wherein
$R^6$ is hydrogen.

Another aspect of the invention are compounds of formula (I), wherein
$R^7/R^8$ is hydrogen or unsubstituted 1-3C-alkyl.

Another aspect of the invention are compounds of formula (I), wherein
$R^7/R^8$ is hydrogen.

Another aspect of the invention are compounds of formula (I), wherein
$R^9$ is hydrogen Another aspect of the invention are compounds of formula (I), wherein
$R^9$ is 1-3C-alkyl, especially methyl or ethyl.

Another aspect of the invention are compounds of formula (I), wherein
$R^{10}$ is hydrogen Another aspect of the invention are compounds of formula (I), wherein
X is —CH$_2$—.

Another aspect of the invention are compounds of formula (I), wherein
Y is —CH$_2$—, —CH(OH)—.

Another aspect of the invention are compounds of formula (I), wherein
Y is —CH$_2$—.

In a further embodiment of the above-mentioned aspects, the invention relates to compounds of formula (I), wherein $R^6$ is hydrogen and $R^5$ is hydrogen.

In another embodiment of the above-mentioned aspects, the invention relates to compounds of formula (I), wherein $R^5$, $R^6$ are hydrogen and $R^4$ is an unsubstituted phenyl ring.

In a further embodiment of the above-mentioned aspects, the invention relates to compounds of formula (I), wherein $R^5$ is hydrogen and $R^4$ is phenyl.

In a further embodiment of the above-mentioned aspects, the invention relates to compounds of formula (I), wherein from $R^1$ and $R^2$ at least one is not hydrogen.

In another embodiment of the above-mentioned aspects, the invention relates to compounds of formula (I), wherein $R^1$ and $R^2$ both are not hydrogen.

Another embodiment of the invention are the compounds of the claims as disclosed in the Claims section wherein the definitions are limited according to the preferred or more preferred definitions as disclosed below or specifically disclosed residues of the exemplified compounds and subcombinations thereof.

DEFINITIONS

Unless defined otherwise in the claims the constituents defined below can optionally be substituted, one or more times, identically or differently, with a substituent selected from:
hydroxy, halogen, cyano, 1-6C-alkyl, 1-4C-haloalkyl, 1-6C-alkoxy, —NR$^7$R$^8$, cyano, (═O), —C(O)NR$^7$R$^8$, —C(O)OR$^9$, —NHC(O)R$^{10}$, —NHS(O)$_2$R$^{10}$. An alkyl constituent being substituted more times by halogen includes also a completely halogenated alkyl moiety such as e.g. CF$_3$.

Should a constituent be composed of more than one part, e.g. —O-(1-6Calkyl)-(3-7C)-cycloalkyl, the position of a possible substituent can be at any of these parts at any suitable position. A hyphen at the beginning of the constituent marks the point of attachment to the rest of the molecule. Should a ring be substituted the substitutent could be at any suitable position of the ring, also on a ring nitrogen atom.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

"1-6C-alkyl" is a straight-chain or branched alkyl group having 1 to 6 carbon atoms. Examples are methyl, ethyl, n propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Those parts of constituents containing an alkyl chain as a bridging moiety between two other parts of the constituent which usually is called an "alkylene" moiety is defined in line with the definition for alkyl above including the preferred length of the chain e.g. methylen, ethylene, n-propylen, iso-propylen, n-butylen, isobutylene, tert-butylen.

"Mono- or di-1-4C-alkylamino" radicals contain in addition to the nitrogen atom, independently one or two of the above mentioned 1-4C-alkyl radicals. Examples are the methyamino, the ethylamino, the isopropylamino, the dimethylamino, the diethylamino and the diisopropylamino radical.

"Halogen" within the meaning of the present invention is iodine, bromine, chlorine or fluorine, preferably "halogen" within the meaning of the present invention is chlorine or fluorine, in the sense of $R^2$ it is bromine, should a halogen atom be needed as leaving group within the synthesis iodine or bromine are preferred.

"1-4C-Haloalkyl" is a straight-chain or branched alkyl group having 1 to 4 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl, whereby fluoromethyl, difluoromethyl, trifluoromethyl, fluoroethyl, 1,1-difluoroethyl, or 1,1,1-trifluoroethyl are preferred. Partially or completely fluorinated C1-C4-alkyl groups are considered to be encompassed by the term 1-4C-haloalkyl.

"1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, iso butoxy, sec-butoxy, tert-butoxy, propoxy, isopropoxy, ethoxy and methoxy radicals, preferred are methoxy, ethoxy, propoxy, isopropoxy.

"3-7C-Cycloalkyl" stands for cyclopropyl, cyclobutyl, cyclopentyl, cyclohexyl or cycloheptyl, preferably cyclopropyl.

"3-7C-Heterocyclyl", or "heterocyclyl" represents a mono- or polycyclic, preferably mono- or bicyclic, more preferably monocyclic, nonaromatic heterocyclic radical containing, 4 to 10, preferably 4 to 7, ring atoms, and up to 3, preferably up to 2, hetero atoms and/or hetero groups from the series consisting of N, O, S, SO, $SO_2$. The heterocyclyl radicals can be saturated or partially unsaturated and, unless stated otherwise, may be optionally substituted, one or more times, identically or differently, with a substituent selected from: 1-4C-alkyl, 1-4C-haloalkyl, 1-4C-alkoxy, hydroxy, fluorine or (=O) whereby the 1-4C-alkyl may be optionally further substituted with hydroxy and the double bonded oxygen atom leads to a carbonyl group together with the carbon atom of the heterocyclyl ring at any suitable position. Particularly preferred heterocyclic radicals are 4- to 7-membered monocyclic saturated heterocyclyl radicals having up to two hetero atoms from the series consisting of O, N and S. The following may be mentioned by way of example and by preference: oxetanyl, tetrahydrofuranyl, azetidinyl, 3-hydroxyazetidinyl, 3-fluoroazetidinyl, 3,3-difluoroazetidinyl, pyrrolidinyl, 3-hydroxypyrrolidinyl, pyrrolinyl, piperidinyl, 3-hydroxypiperidinyl, 4-hydroxypiperidinyl, 3-fluoropiperidinyl, 3,3-difluoropiperidinyl, 4-fluoropiperidinyl, 4,4-difluoropiperidinyl, piperazinyl, N-methylpiperazinyl, N-(2-hydroxyethyl)-piperazinyl, morpholinyl, thiomorpholinyl, azepanyl, homopiperazinyl, N-methyl-homopiperazinyl.

The $NR^7R^8$ group includes, for example, $NH_2$, $N(H)CH_3$, $N(CH_3)_2$, $N(H)CH_2CH_3$ and $N(CH_3)CH_2CH_3$ preferred is $NH_2$.

In the case of —$NR^7R^8$, when $R^7$ and $R^8$ together with the nitrogen atom to which they are attached form a saturated or unsaturated 3-6C-heterocyclic ring, the term "3-6C-heterocyclic ring" includes all saturated or unsaturated non-arylic heterocyclic rings containing 4 to 7 ring atoms and having 1 or 2 nitrogen atoms, or 1 nitrogen atom and 1 oxygen atom. The 3-6C-heterocyclic ring may be optionally substituted one or more times, identically or differently, with a substituent selected from: 1-4C-alkyl, 1-4C-haloalkyl, 1-4C-alkoxy, hydroxy, fluorine, or (=O)—an oxygen atom being connected via a double bond to a carbon atom of the ring thus forming a carbonyl group which can be positioned besides the nitrogen atom resulting in a lactame moiety or at any other carbon atom of the ring, whereby the 1-4C-alkyl may be optionally further substituted with hydroxy. Preferred examples are azetidine, 3-hydroxyazetidine, 3-fluoroazetidine, 3,3-difluoroazetidine, pyrrolidine, pyrrolidin-2-one, 3-hydroxypyrrolidine, piperidine, 3-hydroxypiperidine, 4-hydroxypiperidine, 3-fluoropiperidine, 3,3-difluoropiperidine, 4-fluoropiperidine, 4,4-difluoropiperidine, 1H-pyridine-2-one, piperazine, N-methyl-piperazine, N-(2-hydroxyethyl)-piperazine, morpholine.

"Aryl" represents a mono-, or bicyclic aromatic carbocyclic radical having, as a rule, 6 to 10 carbon atoms; by way of example phenyl or naphthyl. Phenyl is preferred. The aryl moiety can be substituted one or more times, identically or differently by hydroxy, halogen, cyano, 1-6C-alkyl, 1-4C-haloalkyl, 1-6C-alkoxy, —$NR^7R^8$, cyano, —$C(O)NR^7R^8$, —$C(O)OR^9$, —$NHC(O)R^{10}$, —$NHS(O)_2R^{10}$. In one embodiment of the invention if the phenyl moiety were a substitutent it is not substituted or only substituted once.

The term "heteroaryl" represents a monocyclic 5- or 6-membered aromatic heterocycle or a fused bicyclic aromatice moiety comprising without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl as well as the fused ring systems such as e.g. phthalidyl-, thiophthalidyl-, indolyl-, isoindolyl-, dihydroindolyl-, dihydroisoindolyl-, indazolyl-, benzothiazolyl-, benzofuranyl-, benzimidazolyl-, benzoxazinonyl-, chinolinyl-, isochinolinyl-, chinazolinyl-, chinoxalinyl-, cinnolinyl-, phthalazinyl-, 1,7- or 1,8-naphthyridinyl-. cumarinyl-, isocumarinyl-, indolizinyl-, isobenzofuranyl-, azaindolyl-, azaisoindolyl-, furanopyridyl-, furanopyrimidinyl-, furanopyrazinyl-, furanopyidazinyl-, preferred fused ring system is indazolyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The NH(CO)$R^{10}$ group includes for example NH(CO)CH$_3$, NH(CO)C$_2$H$_5$, NH(CO)C$_3$H$_7$, NH(CO)CH(CH$_3$)$_2$.

The NHS(O)$_2$$R^{10}$ group includes for example NHS(O)$_2$CH$_3$, NHS(O)$_2$C$_2$H$_5$, NHS(O)$_2$C$_3$H$_7$, NHS(O)$_2$CH(CH$_3$)$_2$.

The C(O)$NR^7R^8$ group includes, for example, C(O)NH$_2$, C(O)N(H)CH$_3$, C(O)N(CH$_3$)$_2$, C(O)N(H)CH$_2$CH$_3$, C(O)N(CH$_3$)CH$_2$CH$_3$ or C(O)N(CH$_2$CH$_3$)$_2$. In the case of —$NR^7R^8$, when $R^7$ and $R^8$ together with the nitrogen atom to which they are attached form a 3-6C-heterocyclic ring, the term "3-6C-heterocyclic ring" is defined above.

The C(O)$OR^8$ group includes for example C(O)OH, C(O)OCH$_3$, C(O)OC$_2$H$_5$, C(O)OC$_3$H$_7$, C(O)CH(CH$_3$)$_2$, C(O)OC$_4$H$_9$, C(O)OC$_5$H$_{11}$, C(O)OC$_6$H$_{13}$; for C(O)O(1-6Calkyl) the alkyl part may be straight or branched.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Constituents which are optionally substituted as stated herein, may be substituted, unless otherwise noted, one or more times, independently from one another at any possible position. When any variable occurs more than one time in any constituent, each definition is independent.

In case of $R^1$ or $R^2$ it is understood that the groups selected from 1-6C-alkyl, 1-6C-alkoxy, may be optionally substituted, one or more times, identically or differently, with a substituent selected from: hydroxy, halogen, 1-6C-alkyl, 1-4C-haloalkyl, 1-6C-alkoxy, —$NR^7R^8$, cyano, (═O), —C(O)$NR^7R^8$, —C(O)$OR^9$, —NHC(O)$R^{10}$, —NHS(O)$_2$$R^{10}$, heteroaryl, preferred in the sense of the invention is that the groups selected from 1-6C-alkyl, 1-6C-alkoxy are unsubstituted.

The heteroarylic, heteroarylenic, or heterocyclic groups mentioned herein may be substituted by their given substituents or parent molecular groups, unless otherwise noted, at any possible position, such as e.g. at any substitutable ring carbon or ring nitrogen atom. Analogously it is being understood that it is possible for any heteroaryl or heterocyclyl group to be attached to the rest of the molecule via any suitable atom if chemically suitable. Unless otherwise noted, any heteroatom of a heteroarylic or heteroarylenic ring with unsatisfied valences mentioned herein is assumed to have the hydrogen atom(s) to satisfy the valences. Unless otherwise noted, rings containing quaternizable amino- or imino-type ring nitrogen atoms (—N═) may be preferably not quaternized on these amino- or imino-type ring nitrogen atoms by the mentioned substituents or parent molecular groups.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from NH$_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below, as well as their use for the synthesis of the compounds of claims 1-5, are one further aspect of the present invention. Preferred intermediates are the Intermediate Examples as disclosed below.

The Compounds According to the Invention can be Prepared as Follows.

The compounds according to the invention can be prepared according to the following Scheme 1, Scheme 1:

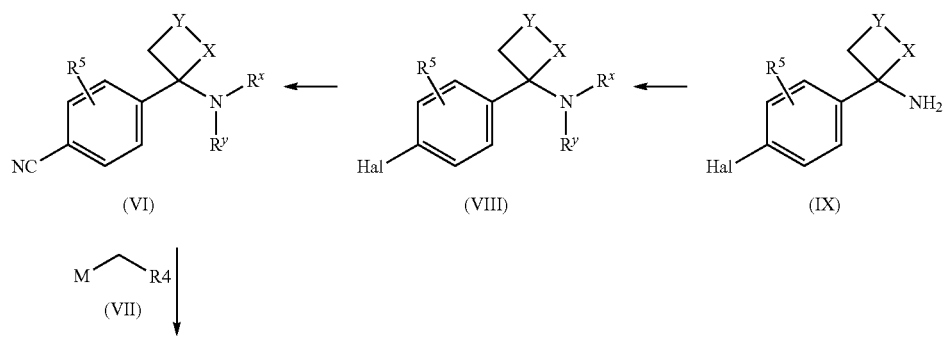

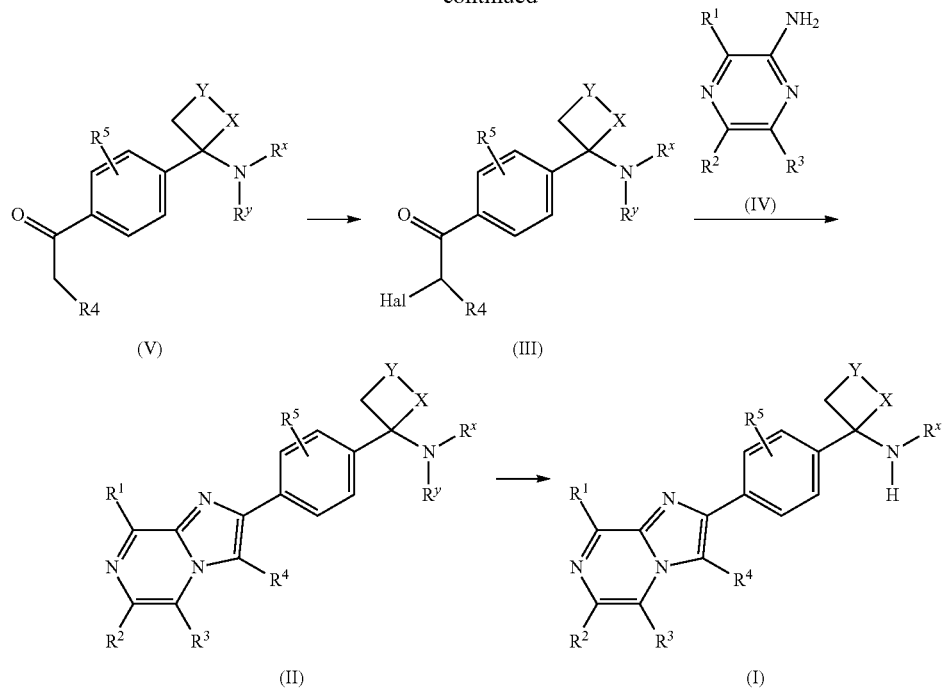

wherein X, Y, R$^1$, R$^2$, R$^3$, R$^4$, R$^5$ and R$^6$ have the meanings defined above and in the claims, whereby R$^x$ has the meaning of R$^6$ and may also be a protecting group; R$^y$ is H, or a protecting group, whereby R$^x$ and R$^y$ together, or Y and R$^x$ together, may form a cyclic protecting group; Hal is halogen, preferably Cl, Br, or I; M is a metal moiety, such as —Li, —MgCl, —MgBr.

Compounds of general formula (I) may be prepared from compounds of general formula (II). Ry may optionally be R$^6$, or a protecting group, or other such precursor which requires further manipulation. For example, R$^x$ in compounds of general formula (II) may be a protecting group such as the Boc group, —CO(OtBu). Thus in special embodiment of the invention the protecting group is a Boc group. Preparation of compounds of general formula (I) may thus be accomplished by use of an appropriate deprotection reaction, such as in the case of a Boc group, acidic reaction conditions, for example, with a solution of 4M hydrogen chloride in dioxane, in an appropriate solvent, such as for example DCM and methanol, at ambient temperature. The resulting ammonium salts are usually converted to the free amines by using, e.g., bases known to the skilled person, e.g., bicarbonate, amine bases such as Hunig's base (diisopropylethylamine), sodium hydroxide, ammonia, or by eluting the compounds with methanol/ammonia from a PoraPak™ column. Further conditions to deprotect the Boc group, or further protecting groups that may be suitable for use in blocking the amino functionality in compounds of general formula (II), including their synthesis and deprotection, are found, for example, in T. W. Greene, Protective Groups in Organic Synthesis, John Wiley & Sons, 1999, 3rd Ed., or in P. Kocienski, Protecting Groups, Thieme Medical Publishers, 2000. Similarly, when R$^y$ is not H, then Ry is a protecting group, such as for example when R$^x$ and R$^y$ together form a cyclic protecting group such as for example a phthalamide.

Furthermore, compounds of general formula (II) may contain functionality that may itself be further modified, thus allowing introduction of the desired functionality in the R$^1$ or R$^2$ groups. Such transformations include oxidations, reductions, nucleophilic substitutions, electrophilic substitutions, radical reactions, or metal promoted reactions such as metal assisted cross-coupling reactions, such as for example Suzuki, Stille, or Heck reactions, or the like. Similarly, compounds of general formula (I) may also be modified in this way to provide further compounds according to the invention, providing the transformations do not cause unwanted side reactions at the —NHR$^6$ group.

Compounds of general formula (II) may be prepared from an intermediate ketone of general formula (III) and a heterocyclic amine of general formula (IV), by use of an appropriate cyclisation reaction. For example, compounds of general formula (II) may be prepared by reacting (III) and (IV) in an appropriate solvent, such as for example DMF, butyronitrile, ethanol or isopropanol, at elevated temperatures from 50° C. to 150° C. The use of basic additives such as a tertiary amine, for example triethylamine or diisopropylamine, or additives such as molecular sieves may be beneficial.

Compounds of general formula (IV) are either commercially available, may be prepared using the methods described in the examples, may be prepared using known methods, or may be prepared by analogous methods to those known by the person skilled in the art.

Compounds of general formula (III) may be prepared from a ketone of general formula (V) by use of an appropriate halogenation reaction. For example in the case of halogen is Br, a suitable bromination reaction, such as for example by reacting a ketone of general formula (V) with pyridinium hydrobromide perbromide in a suitable solvent, such as THF, at suitable temperatures, such as for example from 0° C. to ambient temperature.

Compounds of general formula (V) may be prepared from a compound of general formula (VI) using known methods, such as by addition of a suitable organometallic reagent (VII), in a suitable solvent, such as ethereal solvents, for example THF, at low temperatures, for example from −78° C. to −10° C., preferably from −30° C. to −10° C. Preferred organometallic reagents are for ex ample organomagnesium reagents in which M is —MgCl or —MgBr, more preferably —MgCl.

Compounds of general formula (VI) may be prepared from compounds of general formula (VIII) using known methods, such as by way of a palladium catalysed cyanation reaction, using a suitable catalyst such as tetrakis(triphenylphosphine)palladium(0)[Pd(PPh$_3$)$_4$], a suitable cyano source, such as zinc dicyanide, a suitable solvent, such as DMF, whereby dry DMF may be beneficial, and elevated temperatures, such as up to the boiling point of the solvent, preferably at 80° C.

Compounds of general formula (VIII) and (IX) are either commercially available, may be prepared using the methods described below, may be prepared using known methods, or may be prepared by analogous methods to those known by the person skilled in the art.

Thus one aspect of the invention is the process for the manufacture of compounds of general formula (I), characterized in that a compound of formula (III)

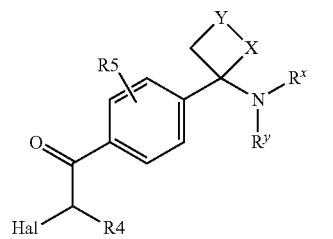

(III)

whereby $R^4$, $R^5$ and $R^6$, X and Y have the meaning according to claim 1 and $R^x$ is $R^6$ or a protecting group; Ry is hydrogen or a protecting group, or $R^x$ and $R^y$ together, or Y and $R^x$ together, may form a cyclic protecting group, Hal is halogen,
is reacted with a compound of formula (IV)

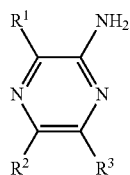

(IV)

whereby $R^1$, $R^2$ and $R^3$ have the meaning according to claim 1,
forming a compound of formula (II)

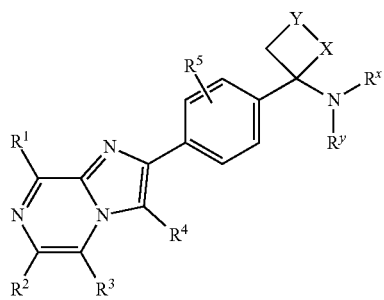

(II)

is optionally subsequently deprotected to form a compound of general formula (I).

One preferred aspect of the invention is the process for the manufacture of the compounds of claims 1-5 according to the Examples.

Another aspect of the invention is the intermediate of general formula (III)

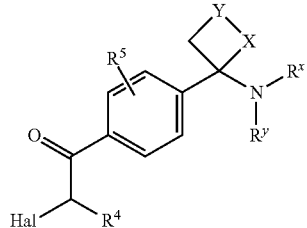

(III)

wherein $R^4$, $R^5$ and $R^6$, X and Y have the meaning according to claim 1 and $R^x$ is $R^6$ or a protecting group; $R^y$ is hydrogen or a protecting group, or $R^x$ and $R^y$ together, or Y and $R^x$ together, may form a cyclic protecting group, Hal is halogen as well as its use for the production of the compounds of general formula (I).

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as metachloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt). An abnormal activation of the PI3K/AKT pathway is an essential step towards the initiation and maintenance of human tumors and thus its inhibition, for example with AKT inhibitors, is understood to be a valid approach for treatment of human tumors. For a recent review see Garcia-Echeverria et al (Oncogene, 2008, 27, 551-5526).

Cellular activity and analogous terms in the present invention is used as known to persons skilled in the art, as an example, inhibition of phosphorylation, inhibition of cellular proliferation, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which executes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Furthermore, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of the Pi3K/Akt pathway induces cellular effects as mentioned herein, alone, or in combination with standard cytotoxic or targeted cancer drugs.

In addition inhibition of AKT signaling pathway was found to inhibit retinal neovascularisation in the oxygene induced retinopathy model as well as a potential therapeutic use of a AKT inhibition on choroidal neovascularisation was shown (Wang et al., Acta Histochem. Cytochem. 44(2): 103-111, 2011; Yang et al., Investigative Ophthalmology & Visual Science (IOVS), April 2009, Vol. 50, No. 4) These results lead to the conclusion that AKT inhibition could provide a useful therapy for ocular diseases associated with ocular neovascularisation like e.g. AMD, MD und diabetic retinopathy.

Thus one embodiment of the invention includes methods of treatment of ocular diseases associated with ocular neovascular iation especially AMD, MD und diabetic retinopathy comprising administering a compound of general formula (I) as well as the use of those compounds for the treatment of said diseases.

Compounds according to the present invention exhibit anti-proliferative and/or pro-apoptotic and/or chemosensitizing properties. Accordingly, the compounds of the present invention are useful for the treatment of hyperproliferative disorders, in particular cancer. Therefore the compounds of the present invention are useful to induce an anti-proliferative and/or pro-apoptotic and/or chemosensitizing effect in mammals, such as humans, suffering from a hyperproliferative disorders, like cancer.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, especially malignant neoplasia, including cancer and the tumor types as disclosed below.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are useful for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The invention further includes as a preferred embodiment methods for treatment of melanoma, NSCLC, brain-breast- and prostate cancer, more preferred breast cancer, comprising administering a compound of general formula (I) as well as the use of the compounds of general formula (I) for said treatment.

Another aspect of the invention is the use of the compounds of the invention for the treatment of melanoma as well as methods for treatment of melanoma for which the data in view of the publication of O'Reilly et al. (Clin. Cancer Research, 15, 2009, 2872) give a basis.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

Compounds according to the present invention are suitable for treatment, prevention or amelioration of the diseases of benign and malignant behavior as described above, such as e.g. benign or malignant neoplasia, particularly cancer, especially a cancer that is sensitive to Pi3K/Akt pathway inhibition.

The present invention further includes a method for treating, preventing or ameliorating mammals, including humans, preferably treating mammals, including humans, which are suffering from one of the abovementioned conditions, illnesses, disorders or diseases. The method is characterized in that a pharmacologically active and therapeutically effective and tolerable amount of one or more of the compounds according to the present invention is administered to the subject in need of such treatment.

The present invention further includes a method for treating, preventing or ameliorating diseases responsive to inhibition of the Pi3K/Akt pathway, in a mammal, including human, preferably treating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of beningn or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, especially malignant neoplasia, particularly cancer, in a mammal, including human, comprising administering a pharmacologically active and therapeutically effective and tolerable amount of one or more of the compounds according to the present invention to said mammal.

The present invention further includes the use of the compounds of the present invention for the treatment of—as well as a method for treating solid and hematological tumors, whereby solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva, preferably breast tumors. Malignant neoplasias include inherited cancers exemplified by Retinoblastoma and Wilms tumor. In addition, malignant neoplasias include primary tumors in said organs and corresponding secondary tumors in distant organs ("tumor metastases"). and hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The present invention further relates to the use of the compounds for the production of pharmaceutical compositions, which are employed for the treatment, prophylaxis, and/or amelioration of one or more of the illnesses mentioned, preferably for the treatment of one or more of the illnesses mentioned.

The present invention further relates to the use of the compounds for the manufacture of pharmaceutical compositions for treating, preventing or ameliorating, preferably treating hyperproliferative diseases and/or disorders responsive to the induction of apoptosis, such as e.g. beningn or malignant neoplasia, especially malignant neoplasia, in particular cancer, especially those cancer diseases and tumor types mentioned above, especially breast cancer.

The present invention further relates to the use of the compounds according to this invention for the production of pharmaceutical compositions for treating, preventing or ameliorating, preferably treating benign or malignant neoplasia, especially malignant neoplasia, particularly cancer, such as e.g. any of those cancer diseases and tumor types described above.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The invention further related to the use of a compound according to the invention or a pharmaceutically acceptable salt thereof, for the production of a pharmaceutical composition for the treatment, prevention or amelioration of a disease mediated by a dysregulated function of a single protein kinase or multiple protein kinases and/or disorders responsive to the induction of apoptosis.

The invention further relates to a pharmaceutical composition, comprising a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, trans-dermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1500 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range depending from the agent combined.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. beningn or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating, especially treating hyperproliferative diseases and/or disorders responsive to induction of apoptosis, such as e.g. benign or malignant neoplasia, especially malignant neoplasia, e.g. cancer, particularly any of those cancer diseases and tumor types mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating, especially treating hyperproliferative diseases, and/or disorders responsive to the induction of apoptosis, such as e.g. malignant or benign neoplasia, especially malignant neoplasia, such as e.g. cancer, particularly those diseases and tumor types mentioned herein.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially malignant neoplasia, e.g. cancer, like any of those cancer diseases and tumor types mentioned herein.

In addition, compounds according to the present invention can be used in the pre- or post-surgical treatment of cancer.

In further addition, compounds of the present invention can be used in combination with radiation therapy.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Experimental Part

The following table lists the abbreviations used in this paragraph and in the Intermediate Examples and Examples section as far as they are not explained within the text body. A comprehensive list of the abbreviations utilized by organic chemists of ordinary skill in the art appears presented in the first issue of each volume of the *Journal of Organic Chemistry*; this list is typically presented in a table entitled Standard List of Abbreviations. The abbreviations contained therein, and all abbreviations utilized by organic chemists of ordinary skill in the art are hereby incorporated by reference. NMR peak forms are stated as they appear in the spectra, possible higher order effects have not been considered.

| Abbreviation | Meaning |
|---|---|
| boc | tert-butoxycarbonyl |
| br | broad |
| CI | chemical ionisation |
| d | doublet |
| dd | doublet of doublet |
| DAD | diode array detector |
| DCM | dichloromethane |
| EtOAc | ethyl acetate |
| eq | equivalent |
| ESI | electrospray (ES) ionisation |
| HPLC | high performance liquid chromatography |
| LC-MS | liquid chromatography mass spectrometry |
| m | multiplet |
| MS | mass spectrometry |
| NMR | nuclear magnetic resonance spectroscopy |
| q | quartet |
| r.t. or rt | room temperature |
| RT | retention time |
| s | singlet |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

EXAMPLES

UPLC-MS Standard Procedures

Analytical UPLC-MS was performed using UPLC-MS Method 1 unless otherwise stated. The masses (m/z) are reported from the positive mode electrospray ionisation unless the negative mode is indicated (ES−).

UPLC-MS Method 1

Instrument: Waters Acquity UPLC-MS SQD 3001; column: Acquity UPLC BEH C18 1.7 50×2.1 mm; eluent A: water+0.1% formic acid, eluent B: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD UPLC-MS Method 2

Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60 t; injection: 2 μl; DAD scan: 210-400 nm; ELSD UPLC-MS Method 3

Instrument: Waters Acquity UPLC-MS SQD 3001; column: Acquity UPLC BEH C18 1.7 50×2.1 mm; eluent A: water+0.1% ammonia, eluent b: acetonitrile; gradient: 0-1.6 min 1-99% B, 1.6-2.0 min 99% B; flow 0.8 mL/min; temperature: 60 t; injection: 2 μl; DAD scan: 210-400 nm; ELSD UPLC-MS Method 4 instrument: Waters Acquity UPLC-MS SQD 3001; column: Acquity UPLC BEH C18 1.7 50×2.1 mm; eluent A: water+0.2% ammonia, eluent B: acetonitrile; gradient: 0-1.6 min 1-99% B, 1.6-2.0 min 99% B; flow 0.8 mL/min; temperature: 60° C.; injection: 2 μl; DAD scan: 210-400 nm; ELSD UPLC-MS Method 5 instrument: Waters Acquity UPLC-MS SQD; column: Acquity UPLC BEH C18 1.7 50×2.1 mm; eluent A: Wasser+ 0.2% Vol. ammonia (32%), eluent B: acetonitrile; gradient: 0-1.6 min 1-99% B, 1.6-2.0 min 99% B; flow 0.8 mL/min; temperature: 60° C.; injection: 2 μl; DAD scan: 210-400 nm; ELSD

INTERMEDIATE EXAMPLES

Intermediate Example Int-1 tert-Butyl {1-[4-(8-methoxy-3-phenylimidazo[1,2-a] pyrazin-2-yl)phenyl]-cyclobutyl}carbamate

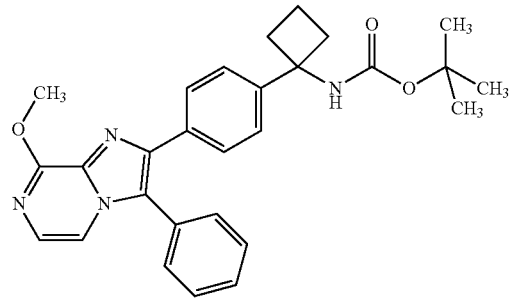 [SMILES: COc1nccn2c(-c3ccccc3)c(-c3ccc(C4(NC(=O)OC(C)(C)C)CCC4)cc3)nc12]

Step 1: tert-Butyl
[1-(4-bromophenyl)cyclobutyl]carbamate 1-(4-Bromophenyl)cyclobutanamine hydrochloride [CAS 1193389-40-0] (8.99 g, 34.24 mmol, 1.0 eq) was dissolved in DCM and washed sequentially with aqueous sodium bicarbonate and water, and the organic portion was dried and concentrated.

The resulting material was dissolved in dry THF (120 mL) and diisopropylethylamine (17.62 mL, 102.7 mmol, 3.0 eq) under nitrogen, and a solution of di-tert-butyldicarbonate (8.22 g, 37.6 mmol, 1.1 eq) in THF (20 mL) was added. The reaction was stirred at rt overnight. The mixture was partitioned between EtOAc and water and the extracted organic phase was washed with brine and concentrated in vacuo to give the title compound.

Alternatively, the title compound may be prepared by known methods (e.g. WO2008/70041).

Step 2: tert-Butyl
[1-(4-cyanophenyl)cyclobutyl]carbamate

The title compound may be prepared from by known methods, such as those given in WO2008/70041, in particular from tert-butyl [1-(4-bromophenyl)cyclobutyl]-carbamate.

Alternatively, tert-butyl [1-(4-cyanophenyl)cyclobutyl]carbamate (CAS 1032349-97-5) may be obtained commercially.

Step 3: tert-Butyl {1-[4-(phenylacetyl)phenyl]cyclobutyl}carbamate

The title compound may be prepared by known methods, such as those given in WO2008/70041, in particular from tert-butyl [1-(4-cyanophenyl)cyclobutyl]-carbamate.

Step 4: tert-Butyl (1-{4-[bromo(phenyl)acetyl]phenyl}cyclobutyl)carbamate [Int-1A]

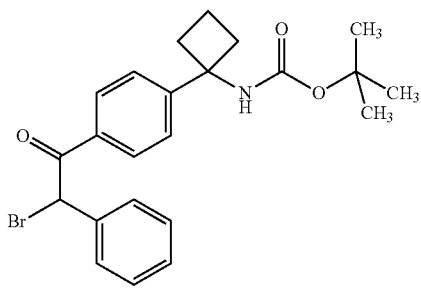 [SMILES: CC(C)(C)OC(=O)NC1(c2ccc(C(=O)C(Br)c3ccccc3)cc2)CCC1]

A mixture of tert-butyl {1-[4-(phenylacetyl)phenyl]cyclobutyl}carbamate (5.0 g, 13.68 mmol, 1.0 eq) and pyridinium hydrobromide perbromide (4.38 g, 13.68 mmol, 1.0 eq) in THF (78 mL) was stirred at 0° C. for 30 minutes. The mixture was partitioned between EtOAc and water, and the organic phase washed with an aqueous sodium thiosulfate solution and brine, dried, filtered through a silicone coated filter paper, and concentrated in vacuo to give the crude title compound (5.44 g, 93% purity by UPLC-MS) which was used without further purification.

UPLC-MS (Method 4): RT=1.49 min; m/z=442 (ES−, M−H, M=$C_{23}H_{26}^{79}BrNO_3$)−.

Step 5: tert-Butyl {1-[4-(8-methoxy-3-phenylimidazo[1,2-a]pyrazin-2-yl)phenyl]cyclobutyl}carbamate [Int-1]

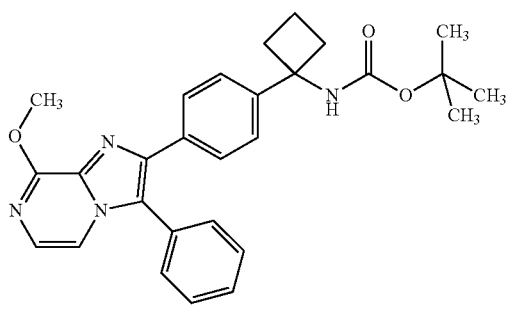 [SMILES: COc1nccn2c(-c3ccccc3)c(-c3ccc(C4(NC(=O)OC(C)(C)C)CCC4)cc3)nc12]

A mixture of crude tert-butyl (1-{4-[bromo(phenyl)acetyl]phenyl}cyclobutyl)carbamate [Int-1-A] (740 mg, 1.67 mmol, 1.0 eq), 3-methoxypyrazin-2-amine (CAS-Nr. 4774-10-1, 417 mg, 3.33 mmol, 2 eq), triethylamine (0.35 mL, 2.50 mmol, 1.5 eq) was dissolved in 24 mL DMF and was heated at 100° C. for 3 hours. On cooling, the mixture was partitioned between ethyl acetate and water, stirred vigorously and the organic phase then was filtered through a silicone coated filter paper. The filtrate was concentrated in vacuo. The crude mixture gave 1.10 g (56% yield) raw product that contained the title compound in 37% purity (UPLC, area-%). The material was forwarded to the next step without further purification.

UPLC-MS (Method 1): RT=1.47 min; m/z=471 (M+H)+.

Intermediate Example Int-2 tert-Butyl {1-[4-(6,8-dimethyl-3-phenylimidazo[1,2-a]pyrazin-2-yl)phenyl]-cyclobutyl}carbamate

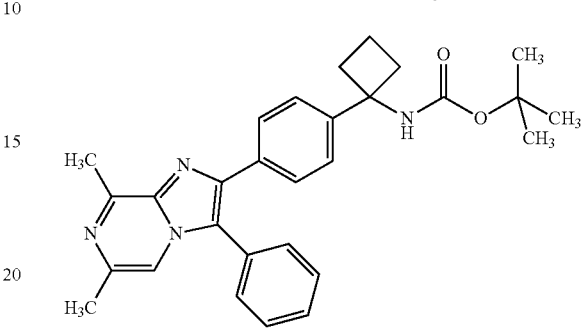

To a mixture of crude tert-butyl (1-{4-[bromo(phenyl)acetyl]phenyl}cyclobutyl)carbamate [Int-1-A] (770 mg, 1.61 mmol, 1.0 eq), 3,5-dimethylpyrazin-2-amine (CAS-Nr. 91678-81-8, 218 mg, 1.77 mmol, 1.1 eq) and diisopropylethylamine (0.28 mL, 1.61 mmol, 1.0 eq) in 10 mL isopropanol was added 3 Å molsieves. The reaction mixture was heated to reflux temperature for 2 h. No conversion was observed under these conditions (UPLC-MS). Therefore, the reaction mixture was heated to 130° C. for 1 h under microwave conditions (single mode microwave oven). The reaction mixture was filtered to remove the molsieve and the filtrate was concentrated in vacuo. The crude mixture was purified via MPLC (Biotage Isolera, 25 g Snap cartridge, DCM→DCM/ethanol 95/5) to deliver 249 mg (31%) of the title compound.

UPLC-MS (Method 1): RT=1.40 min; m/z=469 (M+H)+.

Intermediate Example Int-3 tert-Butyl {1-[4-(6-bromo-8-methoxy-3-phenylimidazo[1,2-a]pyrazin-2-yl)phenyl]cyclobutyl}carbamate

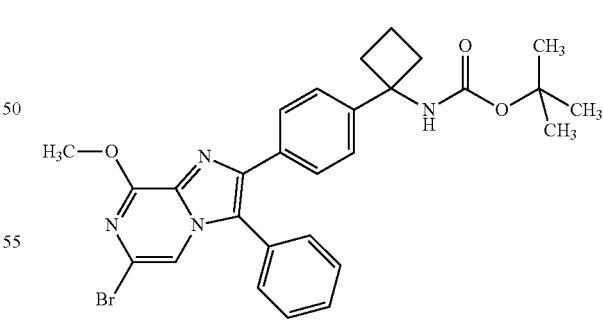

A mixture of crude tert-butyl (1-{4-[bromo(phenyl)acetyl]phenyl}cyclobutyl)carbamate [Int-1-A] (203 mg, 0.38 mmol, 1.0 eq), 5-bromo-3-methoxypyrazin-2-amine (74.6 mg, 0.38 mmol, 1 eq.; Jiang, B. et al. Bioorg. Med. Chem. (2001), 9, 1149-1154.) and diisopropylethylamine (0.064 mL, 0.38 mmol, 1.0 eq) in 2.3 mL butyronitril was heated to 120° C. for 17 hours and to 125° C. for 6 h. The reaction mixture was concentrated in vacuo. The crude mixture was purified via preparative HPLC under basic conditions (column: Waters X-Bridge, eluent: ACN/water (15/85)→ACN/water 55/45) to deliver 9 mg (4%) of the title compound.
UPLC-MS (Method 2): RT=1.62 min; m/z=549 (M)⁺.

Intermediate Example Int-4 tert-Butyl {1-[4-(6-ethyl-8-methoxy-3-phenyl imidazo[1,2-a]pyrazin-2-yl)phenyl]cyclobutyl}carbamate

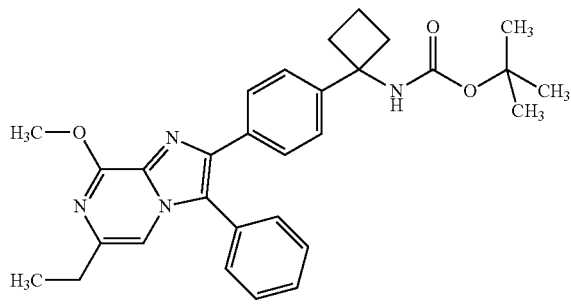 [SMILES: CCc1cn2c(-c3ccccc3)c(-c3ccc(C4(NC(=O)OC(C)(C)C)CCC4)cc3)nc2c(OC)n1]

Step 1: 3-Methoxy-5-vinylpyrazin-2-amine

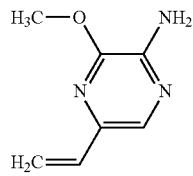

A mixture of 5-bromo-3-methoxypyrazin-2-amine (800 mg, 3.92 mmol, 1 eq.; Jiang, B. et al. Bioorg. Med. Chem. (2001), 9, 1149-1154.), trivinylboroxine pyridine-complex (944 mg, 3.92 mmol, 1.0 eq), tetrakis(triphenylphosphin)palladium(0) (45 mg, 0.04 mmol, 0.01 eq) and potassium carbonate (542 mg, 3.92 mmol, 1.0 eq) in 40 mL dimethoxyethane/water (3/1) was stirred at room temperature for 10 min and then heated to reflux temperature for 3 hours. The reaction mixture was hydrolysed with 100 mL of water and extracted with ethyl acetate. The resulting organic phase was washed with brine, dried with sodium sulphate and concentrated in vacuo. The crude mixture was purified via MPLC (column: Snap cartridge, eluent: hexane→hexane/ethyl acetate 1/1) to deliver 495 mg (78%) of the title compound.
UPLC-MS (Method 2): RT=0.87 min; m/z=152 (M+H)⁺.

Step 2: 5-Ethyl-3-methoxypyrazin-2-amine

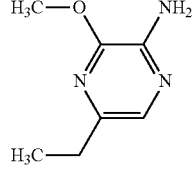

A solution of 3-methoxy-5-vinylpyrazin-2-amine (490 mg, 3.08 mmol; see step 1) in 50 mL ethanol was hydrogenated under atmospheric hydrogen pressure using an H-cube employed with a Pd/C-cartridge. Complete conversion were observed and the volatile components were removed using a rotary evaporator to deliver 500 mg (95%) of the title compound.

¹H-NMR (400 MHz, DMSO-d6): δ [ppm]=1.18 (t, 3H), 2.44 (q, 2H, partially covered by solvent signal), 3.83 (s, 3H), 5.92 (br s, 2H), 7.28 (s, 1H).

Step 3: tert-Butyl {1-[4-(6-ethyl-8-methoxy-3-phenylimidazo[1,2-a]pyrazin-2-yl)phenyl]cyclobutyl}carbamate [Int-4]

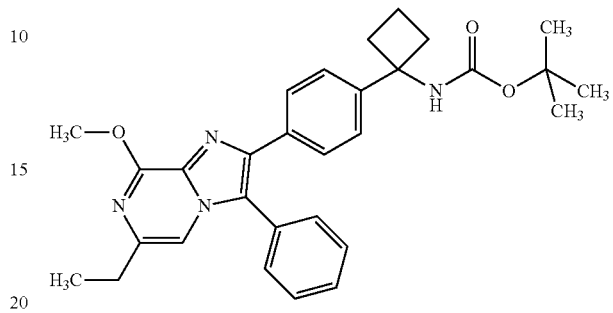

A mixture of crude tert-butyl (1-{4-[bromo(phenyl)acetyl]phenyl}cyclobutyl)carbamate [Int-1-A] (288 mg, 0.55 mmol, 1.0 eq), 5-ethyl-3-methoxypyrazin-2-amine (84.4 mg, 0.55 mmol, 1 eq.; see step 2) and diisopropylethylamine (0.110 mL, 0.61 mmol, 1.1 eq) in 3.9 mL butyronitrile was heated at 120° C. for 20 hours. The reaction mixture was concentrated in vacuo. The crude mixture was purified via MPLC (Isolera, 50 g Snap-cartridge, eluent:hexane→hexane/ethyl acetate 1/1) to deliver 128 mg (25%) of the title compound in approximately 50-60 purity (UPLC). The title compound observed this way was forwarded to the next step without further purification.
UPLC-MS (Method 2): RT=1.64 min; m/z=499 (M+H)⁺.

Intermediate Example Int-5

Ethyl 2-(4-{1-[(tert-butoxycarbonyl)amino]cyclobutyl}phenyl)-3-phenylimidazo[1,2-a]pyrazine-6-carboxylate

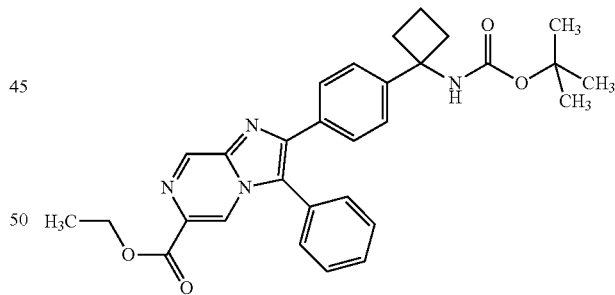

To a mixture of crude tert-butyl (1-{4-[bromo(phenyl)acetyl]phenyl}cyclobutyl)carbamate [Int-1-A] (213 mg, 0.38 mmol, 1.0 eq), ethyl 5-aminopyrazine-2-carboxylate (CAS-Nr. 54013-06-8, 70.5 mg, 0.42 mmol, 1.1 eq.) and diisopropylethylamine (0.055 mL, 0.42 mmol, 1.1 eq) in 2.3 mL butyronitrile was added predried 3 Å mol sieves. The mixture was heated overnight at 120° C. The reaction mixture was partitioned between DCM/water and was filtered through a phase separator. The remaining volatile organic components were removed by the use of a rotary evaporator. In parallel we conducted the same experiment in the absence of diisopropylethylamine following the same protocol. The crude materials of both experiments were combined and purified via MPLC (Biotage Isolera, 25 g Snap-cartridge; eluent: hexane/ethyl acetate (1/1)→ethyl acetate) to deliver 69 mg (14%, yield based on combined amount of tert-butyl (1-{4-[bromo(phenyl)acetyl]-phenyl}cyclobutyl)carbamate) of the title compound.

UPLC-MS (Method 1): RT=1.43 min; m/z=513 (M+H)⁺.

Intermediate Example Int-6

Methyl 2-(4-{1-[(tert-butoxycarbonyl)amino]cyclobutyl}phenyl)-8-methoxy-3-phenylimidazo[1,2-a]pyrazine-6-carboxylate

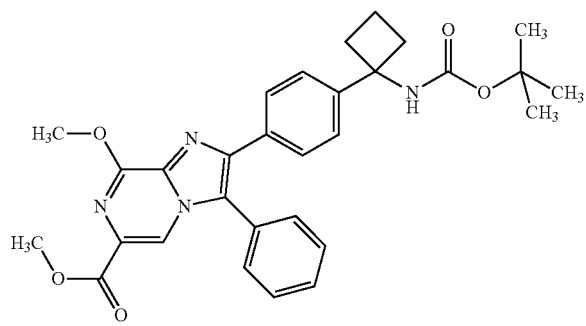 [SMILES: COC(=O)c1cn2c(-c3ccccc3)c(-c3ccc(C4(NC(=O)OC(C)(C)C)CCC4)cc3)nc2c(OC)n1]

Step 1: Methyl 5-amino-6-methoxypyrazine-2-carboxylate

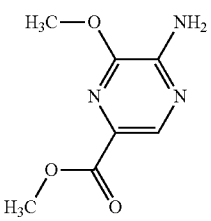

A mixture of 5-bromo-3-methoxypyrazin-2-amine (2.80 g, 13.7 mmol, 1 eq.; Jiang, B. et al. Bioorg. Med. Chem. (2001), 9, 1149-1154), [1,1,-Bis-(diphenylphosphino)ferrocen]palladium(II)-dichlorid (2.24 g, 2.75 mmol, 0.2 eq) and triethylamine (2.10 mL, 15.1 mmol, 1.1 eq) was placed in 600 mL autoclave and dissolved in 135 mL methanol/THF (10/1). The autoclave was flushed with carbon monoxide (3×) and was then pressurized with carbon monoxide to 9 bar. After 30 min at r.t. no conversion was obtained. The autoclave was again pressurized with carbon monoxide to 9 bar and subsequently heated to 100° C. In the course of the reaction, carbon monoxide consumption was observed (decrease of CO pressure). The autoclave was cooled to r.t., flushed with inert gas and the reaction mixture was filtered through a small pad of Celite. LC-MS analysis showed full conversion. The volatile components were removed in vacuo and the material observed this way (1.8 g, 62%) contained the title compound in 92% purity (UPLC-MS, area-%) and was used in the following without further purification.

UPLC-MS (Method 2): RT=0.62 min; m/z=184 (M+H)⁺.

Step 2: Methyl 2-(4-{1-[(tert-butoxycarbonyl)amino]cyclobutyl}phenyl)-8-methoxy-3-phenylimidazo[1,2-a]pyrazine-6-carboxylate

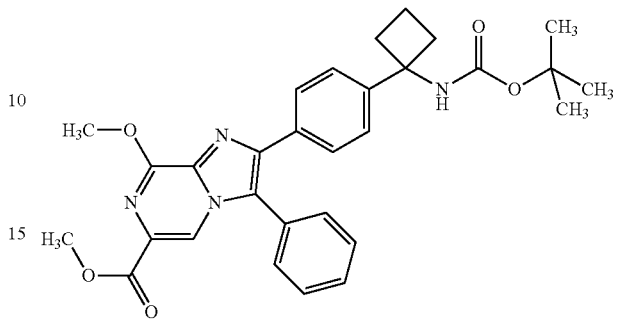

A mixture of crude tert-butyl (1-{4-[bromo(phenyl)acetyl]phenyl}cyclobutyl)carbamate [Int-1-A] (715 mg, 1.45 mmol, 1.0 eq), methyl 5-amino-6-methoxypyrazine-2-carboxylate (265 mg, 1.45 mmol, 1 eq.; see step 1) were dissolved in ethanol. The reaction vessel was equipped with a Dean-Stark trap containing 4 Å molsieves and then the reaction mixture refluxed for 17 h. The reaction mixture was diluted with 20 mL dichloromethane and treated with water. The organic phase was washed with 1 N hydrochloric acid and brine, filtered through a Whatman-filter and the solvent was removed by the use of a rotary evaporator. Finally purification was achieved via MPLC (Isolera, 50 g Snap-cartridge, eluent: hexane→hexane/ethyl acetate 9/1) to deliver 97 mg (12%).

UPLC-MS (Method 2): RT=1.46 min; m/z=529 (M+H)⁺.

Example 1

2-[4-(1-Aminocyclobutyl)phenyl]-3-phenylimidazo[1,2-a]pyrazin-8-ol

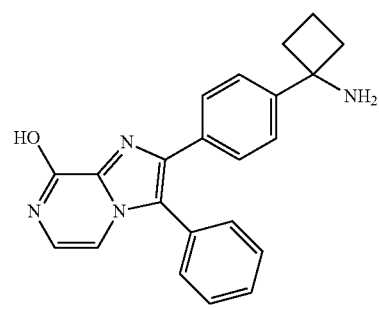 [SMILES: NC1(c2ccc(-c3nc4c(O)nccn4c3-c3ccccc3)cc2)CCC1]

To a mixture of the carbamate Int-1 (1.10 g, 0.940 mmol, purity ~37%, 1.0 eq) in DCM (2.5 mL) and methanol (1.5 mL) was added a solution of 4 M hydrogen chloride in dioxane (4.7 mL, 18.7 mmol, 20.0 eq) and the mixture was stirred overnight at rt. The mixture was poured onto ice, made alkaline with aqueous sodium hydroxide (2 N) and extracted with ethyl acetate. The solvent was removed by distillation and purification was achieved by crystallization from ethyl acetate at 0° C. The resulting solid was collected and dried at high vacuum overnight to give 20 mg (6% yield) of the title compound.

UPLC-MS (Method 1): RT=0.76 min; m/z=355 (ES⁻: M-NH₂)⁻.

$^1$H-NMR (400 MHz, MeOD): δ [ppm]=1.67 (m, 1H), 2.01 (m, 1H), 2.21 (m, 2H), 2.41 (m, 2H), 6.82 (d, 1H), 6.84 (d, 1H), 7.35-7.42 (m, 2H), 7.45-7.54 (m, 4H), 7.55-7.61 (m, 3H).

Example 2

1-[4-(6,8-Dimethyl-3-phenylimidazo[1,2-a]pyrazin-2-yl)phenyl]-cyclobutanamine

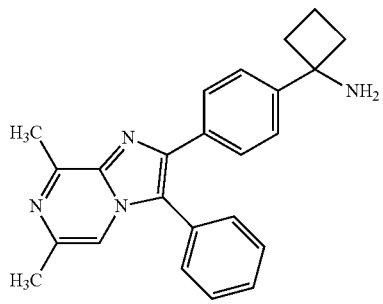 [SMILES: Cc1cn2c(-c3ccccc3)c(-c3ccc(C4(N)CCC4)cc3)nc2c(C)n1]

To a mixture of the carbamate Int-2 (249 mg, 0.53 mmol, 1.0 eq) in DCM (2.0 mL) and methanol (1.3 mL) was added a solution of 4 M hydrogen chloride in dioxane (2.7 mL, 10.6 mmol, 20.0 eq) and the mixture was stirred overnight at rt. The mixture was poured onto ice, made alkaline with aqueous sodium hydroxide (2 N) and extracted with DCM. The solvent was removed by distillation. The crude mixture was purified via MPLC (Biotage Isolera, 25 g Snap cartridge, hexane/ethyl acetate (1/1)→ethyl acetate) to deliver 94 mg (48%) of the title compound.

UPLC-MS (Method 4): RT=1.23 min; m/z=369 (M+H)$^+$.

$^1$H-NMR (400 MHz, DMSO-d6): δ [ppm]=1.58 (m, 1H), 1.85-2.12 (m, 5H), 2.23-2.29 (m, 5H), 2.75 (s, 3H), 7.34 (d, 2H), 7.42-7.62 (m, 7H), 7.69 (s, 1H).

Example 3

1-[4-(6-Bromo-8-methoxy-3-phenylimidazo[1,2-a]pyrazin-2-yl)phenyl]cyclobutanamine

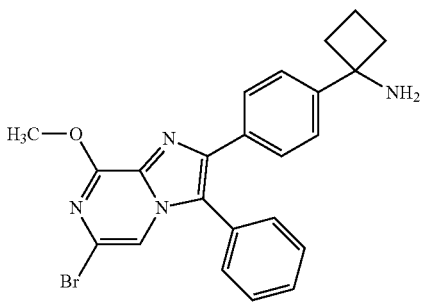 [SMILES: COc1nc(Br)cn2c(-c3ccccc3)c(-c3ccc(C4(N)CCC4)cc3)nc12]

To a mixture of the carbamate Int-3 (~10 mg, 0.02 mmol, 1.0 eq) in DCM (110 μL) and methanol (70 μL) was added a solution of 4 M hydrogen chloride in dioxane (80 μL, 0.33 mmol, 20.0 eq) and the mixture was stirred overnight at rt. The mixture was poured onto ice, made alkaline with aqueous sodium hydroxide (2 N) and extracted with DCM. The aqueous components were removed by filtration through a phase separator. The remaining volatile organic components were removed by the use of a rotary evaporator to deliver 7.8 mg (95%) of the title compound in 90% purity.

UPLC-MS (Method 2): RT=1.41 min; m/z=449 (M)$^+$.

$^1$H-NMR (400 MHz, DMSO-d6): δ[ppm]=1.77 (m, 1H), 4.09 (s, 3H), 7.44 (d, 2H), 7.49 (m, 2H), 7.-56-7.65 (s, 5H), 7.71 (s, 1H), (some protons are covered by solvent signal).

Example 4

1-[4-(6-Ethyl-8-methoxy-3-phenylimidazo[1,2-a]pyrazin-2-yl)phenyl]cyclobutanamine

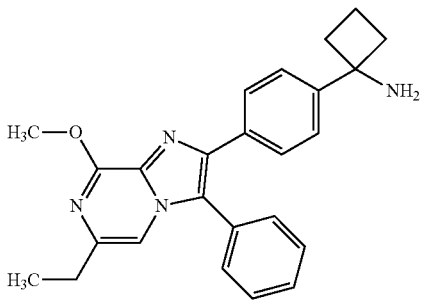 [SMILES: CCc1cn2c(-c3ccccc3)c(-c3ccc(C4(N)CCC4)cc3)nc2c(OC)n1]

To a mixture of the carbamate Int-4 (60 mg, 0.11 mmol, 1.0 eq) in DCM (0.7 mL) and methanol (0.44 mL) was added a solution of 4 M hydrogen chloride in dioxane (0.54 mL, 2.17 mmol, 20.0 eq) and the mixture was stirred overnight at rt. The mixture was poured onto ice, made alkaline with aqueous sodium hydroxide (2 N) and extracted with DCM. The aqueous components were removed by filtration through a phase separator. The remaining volatile organic components were removed by the use of a rotary evaporator. The remaining crude product was purified via MPLC (Biotage Isolera, 10 g Snap-cartridge; eluent: DCM→DCM/ethanol 9:1) to deliver 30 mg (70%) of the title compound.

UPLC-MS (Method 2): RT=1.44 min; m/z=399 (M+1)$^+$.

$^1$H-NMR (400 MHz, DMSO-d6): δ [ppm]=1.15 (t, 3H), 1.60 (m, 1H), 1.85-2.13 (m, 3H), 2.26-2.40 (m, 2H), 2.54 (q, 2H, partially covered by solvents signal), 4.06 (s, 3H), 7.33 (d, 2H), 7.39 (s, 1H), 7.44-7.52 (m, 4H), 7.53-7.63 (m, 3H), (NH$_2$ is not assigned).

Example 5

Ethyl 2-[4-(1-aminocyclobutyl)phenyl]-3-phenylimidazo[1,2-a]pyrazine-6-carboxylate

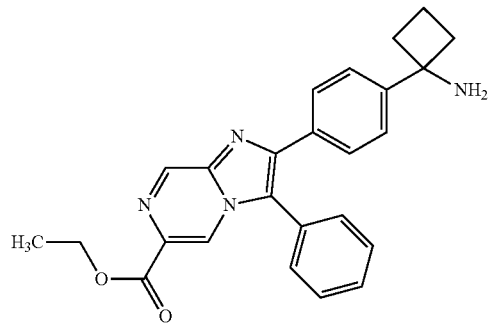 [SMILES: CCOC(=O)c1cn2c(-c3ccccc3)c(-c3ccc(C4(N)CCC4)cc3)nc2cn1]

To a mixture of crude tert-butyl (1-{4-[bromo(phenyl) acetyl]phenyl}cyclobutyl)carbamate [Int-1-A] (245 mg, 0.44 mmol, 1.0 eq) and ethyl 5-aminopyrazine-2-carboxylate (CAS-Nr. 54013-06-8, 81.1 mg, 0.49 mmol, 1.1 eq.) in 2.7 mL butyronitrile was heated at 120° C. for 1.5 h. A substantial amount of the deprotected free amine was detected by UPLC analysis. For isolation, the volatile components were removed using a rotary evaporator and the resulting crude material was purified via MPLC [Biotage Isolera, 25 g Snap-cartridge; eluent: DCM→DCM/ethanol (95/5)] to deliver 38 mg (21%) of the title compound.

UPLC-MS (Method 1): RT=0.90 min; m/z=414 (M+H)$^+$.

$^1$H-NMR (400 MHz, DMSO-d6): δ [ppm]=1.26 (t, 3H), 1.60 (m, 1H), 1.88-2.07 (m, 3H), 2.12 (s br, 2H), 2.26-2.37 (m, 2H), 4.30 (q, 2H), 7.39 (d, 2H), 7.57 (d, 4H), 7.60-7.68 (m, 3H).

Example 6

2-[4-(1-Aminocyclobutyl)phenyl]-3-phenylimidazo [1,2-a]pyrazine-6-carboxamide

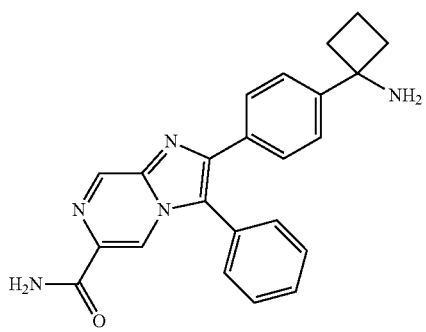 [SMILES: NC(=O)c1cn2c(-c3ccccc3)c(-c3ccc(C4(N)CCC4)cc3)nc2cn1]

A solution of ethyl 2-(4-{1-[(tert-butoxycarbonyl)amino] cyclobutyl}phenyl)-3-phenylimidazo[1,2-a]pyrazine-6-carboxylate [Int-5] (70 mg, 0.14 mmol, 1.0 eq) in 2.0 mL ammonia (7M solution in methanol, ~100 eq) was heated to 130° C. for 5 h in a single mode microwave oven. The volatile components were removed by the use of a rotary evaporator. The crude amide detected by UPLC was directly forwarded to the deprotection step. Therefore, the raw material was dissolved in 1.3 mL DCM/methanol (5/3) and 0.61 mL of 4 M hydrogenchloride in dioxane were added. The solution was stirred overnight at room temperature. The mixture was poured onto ice, made alkaline with aqueous sodium hydroxide (2 N) and extracted with DCM. The combined organic phases were washed with brine and dried with sodium sulphate. The solvent was using a rotary evaporator and the crude material was purified via MPLC (Biotage Isolera, 25 g Snap-cartridge; eluent: hexane/ethyl acetate (1/1)→ethyl acetate) to deliver 20 mg (40%) of the title compound.

UPLC-MS (Method 2): RT=1.01 min; m/z=384 (M+H)$^+$.

$^1$H-NMR (400 MHz, DMSO-d6): δ [ppm]=1.59 (m, 1H), 1.85-2.08 (m, 5H), 2.26-2.38 (m, 2H), 7.39 (d, 2H), 7.52-7.68 (m, 7H), 7.75 (s br, 1H), 8.09 (s br, 1H), 8.39 (d, 1H), 9.13 (d, 1H).

Example 7

Methyl 2-[4-(1-aminocyclobutyl)phenyl]-8-methoxy-3-phenylimidazo[1,2-a]pyrazine-6-carboxylate

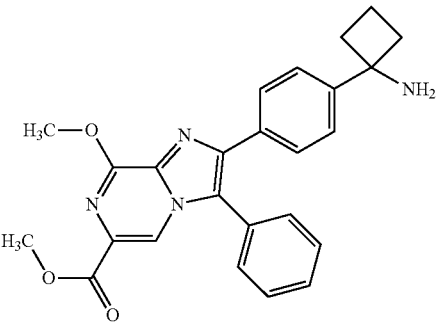 [SMILES: COC(=O)c1cn2c(-c3ccccc3)c(-c3ccc(C4(N)CCC4)cc3)nc2c(OC)n1]

To a mixture of the carbamate Int-6 (97 mg, 0.18 mmol, 1.0 eq) in DCM (1.59 mL) and methanol (1.00 mL) was added a solution of 4 M hydrogen chloride in dioxane (0.80 mL, 3.20 mmol, 17.7 eq) and the mixture was stirred overnight at rt. The mixture was poured onto ice, made alkaline with aqueous sodium hydroxide (2 N) and extracted with DCM. The aqueous components were removed by filtration through a phase separator. The volatile components were removed in vacuo to deliver 51 mg (64%) of the title compound in 97% purity (UPLC-MS, area-%).

UPLC-MS (Method 5): RT=1.21 min; m/z=429 (M+H)$^+$.

$^1$H-NMR (400 MHz, DMSO-d6): δ [ppm]=1.58 (m, 1H), 1.86-2.38 (m, 5H), 3.79 (s, 3H), 4.12 (s, 3H), 7.36 (d, 2H), 7.50-7.57 (m, 4H), 7.58-7.66 (m, 3H), 8.11 (s, 1H).

Example 8

2-[4-(1-Aminocyclobutyl)phenyl]-8-methoxy-3-phenylimidazo[1,2-a]pyrazine-6-carboxamide

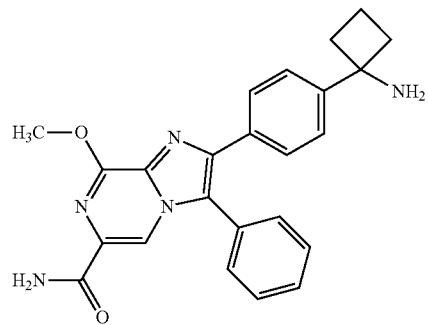 [SMILES: COc1nc(C(N)=O)cn2c(-c3ccccc3)c(-c3ccc(C4(N)CCC4)cc3)nc12]

A solution of methyl 2-[4-(1-aminocyclobutyl)phenyl]-8-methoxy-3-phenylimidazo-[1,2-a]pyrazine-6-carboxylate [Example 7] (65 mg, 0.09 mmol, 80% purity (UPLC area-%), 1.0 eq) in 1.73 mL ammonia (7 M solution in methanol, ~100 eq) was heated to 130° C. for 2 h in a single mode microwave oven. The volatile components were removed by the use of a rotary evaporator. The solvent was using a rotary evaporator and the crude material was purified via MPLC (Biotage Isolera, 10 g Snap-cartridge; eluent: DCM→DCM/ethanol (8/2)) to deliver 22 mg (43%) of the title compound.

UPLC-MS (Method 2): RT=1.03 min; m/z=414 (M+H)+.

$^{1}$H-NMR (400 MHz, MeOD): δ [ppm]=1.74 (m, 1H), 2.06 (m, 1H), 2.24 (m, 2H), 2.54 (m, 2H), 4.28 (s, 3H), 7.39 (d, 2H), 7.49 (dd, 2H), 7.56-7.63 (m, 5H), 8.34 (s, 1H).

Biological Investigations

The following assays can be used to illustrate the commercial utility of the compounds according to the present invention.

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Biological Assay 1.0: Akt1 Kinase Assay

Akt1 inhibitory activity of compounds of the present invention was quantified employing the Akt1 TR-FRET assay as described in the following paragraphs.

His-tagged human recombinant kinase full-length Akt1 expressed in insect cells was purchased form Invitrogen (part number PV 3599). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt1 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt1 in the assay was adjusted depending of the activity of the enzyme lot and was chosen appropriate to have the assay in the linear range, typical enzyme concentrations were in the range of about 0.05 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an in-house software.

Biological Assay 2.0: Akt2 Kinase Assay

Akt2 inhibitory activity of compounds of the present invention was quantified employing the Akt2 TR-FRET assay as described in the following paragraphs.

His-tagged human recombinant kinase full-length Akt2 expressed in insect cells and activated by PDK1 was purchased from Invitrogen (part number PV 3975). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt2 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt2 in the assay was adjusted depending of the activity of the enzyme lot and was chosen appropriate to have the assay in the linear range, typical enzyme concentrations were in the range of about 0.2 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

Preferred compounds of the present invention show in either the Akt1 or Akt2 kinase assay: median $IC_{50}$<5 µM or greater than 50% inhibition at 5 µM, more preferably, median $IC_{50}$<0.5 µM or greater than 50% inhibition at 0.5 µM, even more preferably, median $IC_{50}$≤0.1 µM or greater than 50% inhibition at 0.1 µM.

The following Table gives selected data for selected Examples of the present invention.

| Example | Akt1, median $IC_{50}$, M | Akt2, median $IC_{50}$, M |
| --- | --- | --- |
| 1 | 1.6E−6 | 9.7E−7 |
| 2 | 6.1E−8 | 2.2E−7 |
| 3 | 2.2E−8 | 3.3E−8 |
| 4 | 1.1E−7 | 3.4E−8 |
| 5 | 1.0E−7 | 1.3E−7 |
| 6 | 1.1E−7 | 9.7E−8 |
| 7 | 6.4E−8 | 8.6E−8 |
| 8 | 2.9E−8 | 1.4E−8 |

Cellular Assays 3.0: p-AKT1/2/3-S473, -T308, and p-4E-BP1-T70 assays

The molecular mechanism of action was investigated in a set of experiments to assess the inhibition of the PI3K-AKT-mTOR pathway in responsive cell lines such as KPL-4 breast tumour cell line (PIK3CA$^{H1047R}$, HER2$^{O/E}$ and hormone independent). The phospho-substrates of PI3K-AKT-mTOR axis were used as the readouts to reflect pathway inhibition. Cells were seeded at 60-80% confluency per well in 96-well cell culture plates. After overnight incubation at 37° C. 5% CO2, cells were treated with compounds and vehicle at 37° C. for 2 hours. Thereafter, cells were lysed in 150 µl lysis buffer and the levels of phospho-AKT at T308 and S473 and p-4E-BP1 at T70 sites were determined with the corresponding AlphaScreen® SureFire® assay kits (Perkin Elmer: 4E-BP1 Assay Kit Cat # TRG4E2S10K; Akt 1/2/3 p-Ser 473 #TGRA4S500 and Akt 1/2/3 p-Thr 308 #TGRA3S500 as well as IgG detection Kit #6760617M) as described in the manuals. All measurements where at least done in duplicates and confirmed by independent repetition. Alternatively pAKT-S473 was measured using the "Akt Duplex" of the MULTI-SPOT® Assay System (Fa. Meso Scale Discovery, Cat# N41100B-1) following manufacturers instructions. Each assay used 20 µg of protein extract and measured total AKT and p-AKT content simultaneously in one well. All measurements where at least done in duplicates and confirmed by independent repetition. Values for P-AKT are expressed as percentage of P-AKT level compared to total-AKT content of the extracts.

The following Table gives selected data for selected Examples of the present invention.

| Example | pAKT-S743 median $IC_{50}$, M | P4EBP1-T70 median $IC_{50}$, M |
| --- | --- | --- |
| 1 | not tested | not tested |
| 2 | 2.7E−8 | 1.1E−6 |
| 3 | 1.9E−7 | 1.4E−6 |
| 4 | 8.5E−8 | 3.8E−7 |
| 5 | 3.7E−8 | 2.9E−8 |
| 6 | 2.0E−8 | 1.8E−8 |
| 7 | 4.4E−8 | 4.3E−8 |
| 8 | 7.5E−9 | 1.8E−8 |

Biological Assay 4.0: Tumor Cell Proliferation Assays

Compounds were tested in a cell-based assay that measures the capacity of the compounds to inhibit tumour cell proliferation following a 72 h drug exposure. Cell viability is determined using CellTiter-Glow® (CTG, Promega, cat# G7571/2/3). The CellTiter-Glo® Luminescent Cell Viability Assay is a homogeneous method to determine the number of viable cells in culture. Detection is based on using the luciferase reaction to measure the amount of ATP from viable cells. The amount of ATP in cells correlates with cell viability. Within minutes after a loss of membrane integrity, cells lose the ability to synthesize ATP, and endogenous ATPases destroy any remaining ATP; thus the levels of ATP fall precipitously.

Cells were plated at 3000-5000 cells/well (depending on the cell lines) in 90 µL growth medium on MTPs (Corning; #3603, black plate, clear flat bottom). For each cell line assayed, cells were plated onto a separate plate for determination of fluorescence at t=0 hour and t=72 hour time points. Following overnight incubation at 37° C., chemiluminescence values for the t=0 samples were determined after adding 10 µl medium and 100 µl CTG solution according to manufacture protocol. Plates for the t=72 hour time points were treated with compounds diluted into growth medium at ten times final concentration added in 10 µL to the cell culture plate. Cells were then incubated for 72 hours at 37° C. Chemiluminescence values for the t=72 hour samples were determined. For data analysis, briefly, data from 24 h plate where used to reflect 100% inhibition of growth ("Ci") and DMSO control for uninhibited growth ("C0") and analyzed using MTS software package for $IC_{50}$ and Hill coefficient. Experiments were controlled using a reference compound as standard.

Preferred compounds of the present invention show in this assay an inhibition of cell growth of cell lines such as the KPL-4 breast cancer cell line and the MCF-7 breast tumour cell line (PIK3CA$^{E542K;E545K}$, hormone dependent) with a median $IC_{50}$ of <10 µM, more preferably, median IC50≤1 µM.

The following Table gives selected data for selected Examples of the present invention.

| Example | KPL-4 proliferation $IC_{50}$, M | MCF7 proliferation $IC_{50}$, M | KPL-4 median inhibition at 1.67 µM (%) | MCF-7 median inhibition at 1.67 µM (%) |
| --- | --- | --- | --- | --- |
| 1 | Not tested | Not tested | Not tested | Not tested |
| 2 | 7.1E−7 | 7.2E−7 | 68.0 | 70.8 |
| 3 | 1.7E−6 | 1.7E−6 | 57.0 | 46.2 |
| 4 | 1.2E−6 | 8.5E−7 | 64.4 | 72.4 |
| 5 | 1.0E−5 | 2.4E−6 | 15.2 | 40.6 |
| 6 | 2.9E−7 | 1.1E−6 | 79.5 | 57.3 |
| 7 | 5.5E−6 | 4.2E−7 | 22.0 | 72.3 |
| 8 | 1.5E−7 | 2.7E−7 | 83.6 | 73.1 |

Example 5.0

Caco2 Permeability Assay

Caco-2 cells (purchased from DSMZ Braunschweig, Germany) were seeded at a density of 4.5×10$^4$ cell per well on 24 well insert plates, 0.4 μm pore size, and grown for 15 days in DMEM medium supplemented with 10% fetal bovine serum, 1% GlutaMAX (100×, GIBCO), 100 U/ml penicillin, 100 μg/ml streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by a FCS-free hepes-carbonate transport puffer (pH 7.2) For assessment of monolayer integrity the transepithelial electrical resistance (TEER) was measured. Test compounds were predissolved in DMSO and added either to the apical or basolateral compartment in final concentration of 2 μM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app}=(V_r/P_o)(1/S)(P_2/t)$$

Where $V_r$ is the volume of medium in the receiver chamber, $P_o$ is the measured peak area of the test drug in the donor chamber at t=0, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B-A by the $P_{app}$ A-B. In addition the compound recovery was calculated. As assay control reference compounds were analyzed in parallel.

Example 6.0

In Vivo Rat Pharmacokinetics

For in vivo pharmacokinetic experiments test compounds were administered to male Wistar rats intravenously at doses of 0.3 to 1 mg/kg and intragastral at doses of 0.6 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

The person skilled in the art will be aware of methods to show in vivo efficacy of anti-cancer compounds. By way of illustration, the following example describes methods of quantifying the in vivo efficacy in a mouse xenograft model. The skilled person will be able to apply such principles to derive models from alternative tumor material.

Example 7.0

In Vivo Xenograft Mechanism of Action Study

To demonstrate that compounds act in tumours by the anticipated mode of action phosphorylation of the AKT protein was investigated in KPL-4 breast tumours treated once with 50 mg/kg compound.

To this extent KPL-4 human breast tumours were xenografted onto athymic nude mice. KPL-4 tumour cells were cultivated according to ATCC protocols in recommended media contained 10% FCS and harvested for transplantation in a subconfluent (70%) state. $3 \times 10^6$ tumour cells suspended in 50% Matrigel were subcutaneously implantated into the inguinal region of female mice. Tumours were allowed to grow to the predetermined size of 60-80 $mm^2$. When the tumours were approximately in size, the animals were randomized to treatment and control groups (groups size: 9 animals) and treatment was started. Animals were treated once with 50 mg/kg compound or vehicle per oral administration (p.o.) carried out via a gastric tube. Treatment of each animal was based on individual body weight. At 2, 5 and 24 hours post treatment 3 animals each were sacrificed and the KPL-4 tumours excised. Tumour samples of approximately 5×5×5 mm were lysed on ice in MSD lysis buffer in the presence of protease and phosphatase inhibitors using Tissue Lyzer (Qiagen, Germany). The levels of p-AKT S473 in extracts from tumour tissue were analysed in an ELISA based assay. This assay is based on the "Akt Duplex" of the MULTI-SPOT® Assay System (Fa. Meso Scale Discovery, Cat# N41100B-1) following manufacturers instructions. Each assay used 20 μg of protein extract and measured total AKT and p-AKT content simultaneously in one well. All measurements where at least done in duplicates and confirmed by independent repetition.

Values for P-AKT are expressed as percentage of P-AKT level compared to total-AKT content of the extracts. Vehicle treated tumours were analyzed to determine the basal level of P-AKT in this model and used as a normalization control to determine the % P-AKT relative to vehicle levels.

Preferred compounds of the present invention show in this assay: relative to vehicle levels P-AKT <30% at 2 hours post treatment, more preferably at 5 hours post treatment, even more preferably at 24 hours post treatment.

Example 7.1

In Vivo Xenograft Efficacy Study

To determine the therapeutic efficacy and tolerability of compounds, tumour growth of KPL-4 breast tumours xenografted onto nude mice may be observed. Mice were treated either with vehicle or compounds.

To this extent KPL-4 xenografts were established as described above. Tumours were allowed to grow to the predetermined size of 25-35 mm². When the tumours were approximately in size, the animals were randomized to treatment and control groups (groups size: 8 animals) and treatment was started. Treatment of each animal was based on individual body weight and oral administration (p.o.) was carried out via a gastric tube. The oral application volumes were 10 ml/kg for mice. Mice were treated once daily with 50 mg/kg compounds.

Tumour response was assessed by determination of the tumour area (product of the longest diameter and its perpendicular) using a calliper. The animal body weight was monitored as a measure for treatment-related toxicity. Measurement of tumour area and body weight were performed 2-3 times weekly. Statistical analysis was assessed using the SigmaStat software. A one way analysis of variance was performed, and differences to the control were compared by a pair-wise comparison procedure (Dunn's method). T/C ratios (Treatment/Control) were calculated with final tumour weights at study end.

The invention claimed is:
1. A compound of formula (I)

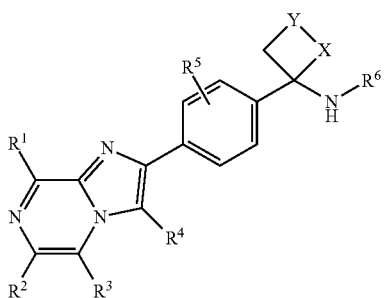

in which
$R^1$ is hydrogen, hydroxy, or
a group selected from 1-6C-alkyl, 1-6C-alkoxy,
wherein said group being optionally substituted, one or more times, identically or differently, with a substituent selected from:
hydroxy, halogen, 1-6C-alkyl, 1-4C-haloalkyl, 1-6C-alkoxy, —$NR^7R^8$, cyano, (=O), —C(O)$NR^7R^8$, —C(O)$OR^9$, —NHC(O)$R^{10}$, —NHS(O)$_2R^{10}$, heteroaryl,
wherein said substituent can be optionally substituted with 1-6C-alkoxy,
$R^2$ is hydrogen, halogen, C(O)$OR^9$, CO($NR^7R^8$), or
a 1-6C-alkyl group
wherein said group is optionally substituted, one or more times, identically or differently, with a substituent selected from:
hydroxy, halogen, 1-6C-alkyl, 1-4C-haloalkyl, 1-6C-alkoxy, —$NR^7R^8$, cyano, —C(O)$NR^7R^8$, —C(O)$OR^9$, —NHC(O)$R^{10}$, —NHS(O)$_2R^{10}$, —NH-(1-6C-alkylen)-O-(1-6C-alkyl),
$R^3$ is hydrogen, 1-6C-alkyl,
$R^4$ is phenyl optionally substituted by 1-6C-alkyl, halogen, cyano,
$R^5$ is hydrogen, halogen,
$R^6$ is hydrogen, 1-6C-alkyl,
X is —CH$_2$—,
Y is —CH$_2$—, —CH(OH)—,
$R^7$, $R^8$ which can be the same or different, is hydrogen, hydroxy, 3-7C-cycloalkyl or a group selected from 1-4C-alkyl, 1-6C-alkoxy, wherein said group is optionally substituted, one or more times, identically or differently, with a substituent selected from:
halogen, hydroxy, mono- or di-(1-4C-alkylamino), 1-4C-alkoxy, or 3-7C-cycloalkyl or,
$R^7$ and $R^8$ together with the nitrogen to which they are attached may also form a saturated or unsaturated 3-6C-heterocyclic ring,
which is optionally substituted by (=O)
$R^9$ is hydrogen, 1-6C-alkyl,
$R^{10}$ is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

2. The compound of formula (I) according to claim 1, wherein
$R^1$ is hydrogen, hydroxy, 1.-6C-alkyl, 1-6C-alkoxy,
$R^2$ is hydrogen, halogen, 1-6C-alkyl, (CO)$OR^9$, (CO)$NR^7R^8$,
$R^3$ is hydrogen,
$R^4$ is phenyl optionally substituted by 1-6C-alkyl, halogen, cyano,
$R^5$ is hydrogen,
$R^6$ is hydrogen,
X is —CH$_2$—,
Y is —CH$_2$—, —CH(OH)—,
$R^7$, $R^8$ which can be the same or different, is hydrogen, hydroxy, or
a group selected from 1-4C-alkyl, 1-6C-alkoxy, wherein said group is optionally substituted, one or more times, identically or differently, with a substituent selected from:
halogen, hydroxy, mono- or di-(1-4C-alkylamino), 1-4C-alkoxy, or 3-7C-cycloalkyl, or,
$R^7$ and $R^8$ together with the nitrogen to which they are attached may also form a saturated or unsaturated 3-6C-heterocyclic ring,
which is optionally substituted by (=O)
$R^9$ is hydrogen, 1-6C-alkyl,
or an N-oxide, a salt, a tautomer or a stereoisomer of said compound, or a salt of said N-oxide, tautomer or stereoisomer.

3. The compound of formula (I) according to claim 1, wherein
$R^1$ is hydrogen, hydroxy, 1.-6C-alkyl, 1-6C-alkoxy,
$R^2$ is hydrogen, halogen, 1-6C-alkyl, (CO)$OR^9$, (CO)$NR^7R^8$,
$R^3$ is hydrogen,
$R^4$ is phenyl
$R^5$ is hydrogen,
$R^6$ is hydrogen,
X is —CH$_2$—,
Y is —CH$_2$—,
$R^7$, $R^8$ which can be the same or different, is hydrogen, 1-4C-alkyl,)
$R^9$ is hydrogen, 1-6C-alkyl,
or an N-oxide, a salt, a tautomer or a stereoisomer of said compound, or a salt of said N-oxide, tautomer or stereoisomer.

4. The compound of formula (I) according to claim 1, wherein,
$R^1$ is hydrogen, hydroxy, 1.-3C-alkyl, 1-3C-alkoxy,
$R^2$ is hydrogen, halogen, 1-3C-alkyl, (CO)O(1-3C-alkyl), (CO)NH$_2$,
$R^3$ is hydrogen,
$R^4$ is phenyl,
$R^5$ is hydrogen,
$R^6$ is hydrogen,
X is —CH$_2$—,
Y is —CH$_2$—,
or an N-oxide, a salt, a tautomer or a stereoisomer of said compound, or a salt of said N-oxide, tautomer or stereoisomer.

5. Compounds of formula (I) according to claim 1, which is selected from the group consisting of:

2-[4-(1-Aminocyclobutyl)phenyl]-3-phenylimidazo[1,2-a]pyrazin-8-ol,

1-[4-(6,8-Dimethyl-3-phenylimidazo[1,2-a]pyrazin-2-yl)phenyl]-cyclobutanamine,

1-[4-(6-Bromo-8-methoxy-3-phenylimidazo[1,2-a]pyrazin-2-yl)phenyl]cyclobutanamine, 1-[4-(6-Ethyl-8-methoxy-3-phenylimidazo[1,2-a]pyrazin-2-yl)phenyl]-cyclobutanamine, Ethyl 2-[4-(1-aminocyclobutyl)phenyl]-3-phenylimidazo[1,2-a]pyrazine-6-carboxylate, 2-[4-(1-Aminocyclobutyl)phenyl]-3-phenylimidazo[1,2-a]pyrazine-6-carboxamide, Methyl 2-[4-(1-aminocyclobutyl)phenyl]-8-methoxy-3-phenylimidazo[1,2-a]-pyrazine-6-carboxylate, and 2-[4-(1-Aminocyclobutyl)phenyl]-8-methoxy-3-phenylimidazo[1,2-a]pyrazine-6-carboxamide, or an N-oxide, a salt, a tautomer or a stereoisomer of said compound, or a salt of said N-oxide, tautomer or stereoisomer.

6. A pharmaceutical composition comprising at least one compound of formula (I) according to claim 1, together with at least one pharmaceutically acceptable auxiliary.

7. A combination comprising one or more first active ingredients selected from a compound of formula (I) according to claim 1, and one or more second active ingredients selected from chemotherapeutic anti-cancer agents.

8. A method for the treatment of breast cancer or benign or malignant neoplasia comprising administering to a mammal in need thereof a therapeutically effective amount of a compound of formula (I) according to claim 1.

\* \* \* \* \*